United States Patent
Stanwood (10) Patent No.: US 10,463,245 B2
(45) Date of Patent: Nov. 5, 2019

(54) METHOD OF USING CANNULA FOR SURGICAL PROCEDURE

(71) Applicant: Snug Harbor Orthopedics, LLC, Duxbury, MA (US)

(72) Inventor: Walter Stanwood, Duxbury, MA (US)

(73) Assignee: Snug Harbor Orthopedics, LLC, Duxbury, MA (US)

( * ) Notice: Subject to any disclaimer, the term of this patent is extended or adjusted under 35 U.S.C. 154(b) by 0 days.

(21) Appl. No.: 15/836,635

(22) Filed: Dec. 8, 2017

(65) Prior Publication Data

US 2018/0098761 A1 Apr. 12, 2018

Related U.S. Application Data

(63) Continuation-in-part of application No. 14/975,875, filed on Dec. 21, 2015, now abandoned.

(51) Int. Cl.
| | | |
|---|---|---|
| A61B 1/317 | (2006.01) | |
| A61B 17/00 | (2006.01) | |
| A61B 1/00 | (2006.01) | |
| A61B 1/018 | (2006.01) | |
| A61B 17/34 | (2006.01) | |

(52) U.S. Cl.
CPC .......... *A61B 1/317* (2013.01); *A61B 1/00066* (2013.01); *A61B 1/00128* (2013.01); *A61B 1/00135* (2013.01); *A61B 1/00142* (2013.01); *A61B 1/00154* (2013.01); *A61B 1/018* (2013.01); *A61B 17/00234* (2013.01); *A61B 17/3421* (2013.01); *A61B 1/0014* (2013.01); *A61B 2017/0034* (2013.01); *A61B 2017/00424* (2013.01); *A61B 2017/347* (2013.01); *A61B 2017/3445* (2013.01)

(58) Field of Classification Search
CPC .............. A61B 1/0008; A61B 1/00087; A61B 1/00101; A61B 1/00112; A61B 1/00135; A61B 1/0014; A61B 1/00142; A61B 1/00154; A61B 1/0125; A61B 2017/00292; A61B 1/317; A61B 17/00234; A61B 17/3421; A61B 2017/00296; A61B 2017/0034; A61B 2017/0042; A61B 2017/00424; A61B 2017/3445; A61B 2017/3447; A61B 1/00066; A61B 1/012; A61B 1/018; A61B 1/313; A61B 1/3132; A61B 1/3135
See application file for complete search history.

(56) References Cited

U.S. PATENT DOCUMENTS

| | | |
|---|---|---|
| 2,071,510 A | 2/1937 | Durrler |
| 2,734,484 A | 2/1956 | O'Sullivan |
| 2,826,173 A | 3/1958 | Gossweiler et al. |
| 2,849,983 A | 9/1958 | Gossweiler et al. |
| 3,084,670 A | 4/1963 | Dottlinger |
| 3,266,465 A | 8/1966 | Ganz |
| 3,819,282 A | 6/1974 | Schultz |

(Continued)

*Primary Examiner* — Ryan N Henderson
(74) *Attorney, Agent, or Firm* — Muir Patent Law, PLLC (57) ABSTRACT

A cannula assembly can allow an operator to control both an endoscope and a surgical tool with a single hand. In some embodiments, for example, a scope tube may be combined with a tool tube to allow such control. The tool may be manipulated, for example, by causing the tool to rotate, and/or to move forward and backward in relation to the cannula assembly.

9 Claims, 9 Drawing Sheets

(56) References Cited

U.S. PATENT DOCUMENTS

| | | | |
|---|---|---|---|
| 4,227,822 A | | 10/1980 | Kokubu |
| 4,268,183 A | | 5/1981 | Sekiguchi |
| 4,741,326 A | * | 5/1988 | Sidall ................ A61B 1/00091 600/123 |
| 4,854,302 A | | 8/1989 | Allred, II |
| 5,259,366 A | * | 11/1993 | Reydel ............... A61B 1/00135 383/203 |
| 5,263,786 A | | 11/1993 | Kageyama |
| 5,290,279 A | | 3/1994 | Bonati et al. |
| 5,637,112 A | | 6/1997 | Moore et al. |
| 5,749,889 A | | 5/1998 | Bacich et al. |
| 6,071,233 A | | 6/2000 | Ishikawa et al. |
| 6,280,110 B2 | | 8/2001 | Lin |
| 6,428,510 B1 | | 8/2002 | Kadan |
| 6,527,753 B2 | | 3/2003 | Sekine et al. |
| 6,786,865 B2 | | 9/2004 | Dhindsa |
| 6,878,106 B1 | | 4/2005 | Herrmann |
| 2003/0130564 A1 | | 7/2003 | Martone et al. |
| 2007/0213585 A1 | | 9/2007 | Monassevitch et al. |
| 2013/0096581 A1 | | 4/2013 | Gilkey et al. |
| 2014/0171735 A1 | * | 6/2014 | Galperin ............ A61B 1/00066 600/106 |
| 2014/0316203 A1 | * | 10/2014 | Carroux ............... A61B 17/221 600/146 |
| 2015/0073215 A1 | * | 3/2015 | Nakajima .......... A61B 1/00135 600/114 |
| 2016/0316998 A1 | | 11/2016 | Lombardi |

\* cited by examiner

FIG. 8

METHOD OF USING CANNULA FOR SURGICAL PROCEDURE

This application is a Continuation-In-Part application of U.S. patent application Ser. No. 14/975,875, filed Dec. 21, 2015, the contents of which are incorporated herein in their entirety by reference.

BACKGROUND

In orthopedic surgery, cannulas provide a channel to insert an instrument or device, such as an arthroscope, through them and subsequently into a joint. This is done via a skin incision called a portal. The vast majority of arthroscopic cannulas used in orthopedics are plastic. They generally range in size from 3-10 mm in diameter. A diaphragm at the proximal end prevents any extravasation of fluid.

The surgeon typically controls the arthroscope, or endoscope, in one hand and in an accessory portal can utilize an instrument with the other hand. At times an assistant may control one of the aforementioned as well. Sometimes it is possible to have two accessory portals, which allows the use of two instruments in a joint at the same time that the arthroscope is being used. However, this is dependent on the surgeon, availability of assistants, the type of case (cuff repair, labral repair, ACL reconstruction, etc.), and the size of the joint. It generally requires at least three hands and three portals, and therefore at least two people, and particularly when in close proximity, this can make certain surgeries and procedures difficult.

SUMMARY

A cannula assembly can allow an operator to control both an endoscope and a surgical tool with a single hand. In some embodiments, for example, a scope tube may be combined with a tool tube to allow such control using a single cannula assembly. The tool may be manipulated, for example, by causing the tool to rotate, and/or to move forward and backward in relation to the cannula assembly. The cannula assembly may therefore reduce the number of holes needed during certain surgeries, and/or may reduce the number of hands needed to perform the surgeries.

In the drawings, the size and relative sizes of layers and regions may be exaggerated for clarity. Like numbers refer to like elements throughout. Though the different figures show variations of exemplary embodiments, these figures are not necessarily intended to be mutually exclusive from each other. Rather, as will be seen from the context of the detailed description below, certain features depicted and described in different figures can be combined with other features from other figures to result in various embodiments, when taking the figures and their description as a whole into consideration.

DETAILED DESCRIPTION

The present disclosure now will be described more fully hereinafter with reference to the accompanying drawings, in which various embodiments are shown. The invention may, however, be embodied in many different forms and should not be construed as limited to the embodiments set forth herein.

The terminology used herein is for the purpose of describing particular embodiments only and is not intended to be limiting of the invention. As used herein, the singular forms "a", "an" and "the" are intended to include the plural forms as well, unless the context clearly indicates otherwise. As used herein, the term "and/or" includes any and all combinations of one or more of the associated listed items and may be abbreviated as "/".

It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

It will be understood that when an element is referred to as being "connected" or "coupled" to or "on" another element, it can be directly connected or coupled to or on the other element or intervening elements may be present. In contrast, when an element is referred to as being "directly connected" or "directly coupled" to another element, there are no intervening elements present. Other words used to describe the relationship between elements should be interpreted in a like fashion (e.g., "between" versus "directly between," "adjacent" versus "directly adjacent," etc.). However, the term "contact," as used herein refers to direct contact (i.e., touching) unless the context indicates otherwise.

It will be understood that, although the terms first, second, third etc. may be used herein to describe various elements, components, regions, layers and/or sections, these elements, components, regions, layers and/or sections should not be limited by these terms. Unless the context indicates otherwise, these terms are only used to distinguish one element, component, region, layer or section from another element, component, region, layer or section, for example as a naming convention. Thus, a first element, component, region, layer or section discussed below in one section of the specification could be termed a second element, component, region, layer or section in another section of the specification or in the claims without departing from the teachings of the present invention. In addition, in certain cases, even if a term is not described using "first," "second," etc., in the specification, it may still be referred to as "first" or "second" in a claim in order to distinguish different claimed elements from each other.

Embodiments described herein will be described referring to plan views and/or cross-sectional views by way of ideal schematic views. Accordingly, the exemplary views may be modified depending on manufacturing technologies and/or tolerances. Therefore, the disclosed embodiments are not limited to those shown in the views, but include modifications in configuration formed on the basis of manufacturing processes. Therefore, regions exemplified in figures have schematic properties, and shapes of regions shown in figures exemplify specific shapes of regions of elements, and the specific properties and shapes do not limit aspects of the invention.

Spatially relative terms, such as "beneath," "below," "lower," "above," "upper" and the like, may be used herein for ease of description to describe one element's or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the term "below" can encompass both an orientation of above and below. The device may be otherwise oriented (rotated 90 degrees or at other orientations) and the spatially relative descriptors used herein interpreted accordingly.

Terms such as "same," "planar," or "coplanar," as used herein when referring to orientation, layout, location, shapes, sizes, amounts, or other measures do not necessarily mean an exactly identical orientation, layout, location, shape, size, amount, or other measure, but are intended to encompass nearly identical orientation, layout, location, shapes, sizes, amounts, or other measures within acceptable variations that may occur, for example, due to manufacturing processes. The term "substantially" may be used herein to reflect this meaning.

Unless otherwise defined, all terms (including technical and scientific terms) used herein have the same meaning as commonly understood by one of ordinary skill in the art to which this disclosure belongs. It will be further understood that terms, such as those defined in commonly used dictionaries, should be interpreted as having a meaning that is consistent with their meaning in the context of the relevant art and/or the present application, and will not be interpreted in an idealized or overly formal sense unless expressly so defined herein.

The various embodiments described herein relate to a surgical apparatus that allows for both an endoscope and a surgical tool to be manipulated by the same hand of an operator. In this manner, the second hand of the operator is free to hold and manipulate a second tool or object, to perform certain surgical or diagnostic procedures that in the prior art would have required three hands and thus an additional person (e.g., a technician, assistant, or second operator).

Figure 1:
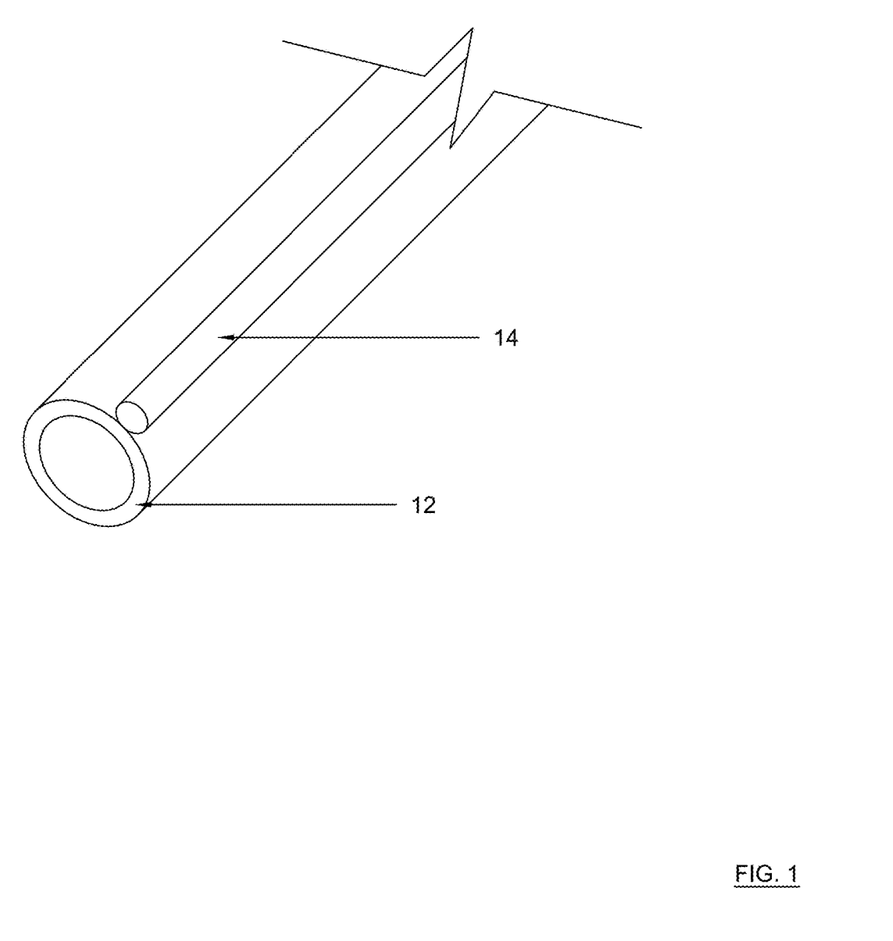
FIG. 1 depicts a portion of a surgical apparatus according to certain exemplary embodiments.

According to various aspects of the disclosed embodiments, the surgical apparatus includes a cannula assembly (also referred to herein as a cannula), which may have two parts that are used together for certain procedures. The parts may include, for example, two tubes that may be connected to each other. As such, there may be two lumens formed by the two tubes. FIG. 1 depicts a portion of a surgical apparatus 10, including an example of a first tube 12 having a first lumen and a second tube 14 having a second lumen. A first lumen may be configured to house an endoscope, and may have part of an endoscope inserted therein. The endoscope, may include, for example, a rigid or flexible tube, a light delivery system to illuminate light onto an object, a lens system which may include a lens at an end of a fiber optic cable in addition to other optical elements, and an image capture device such as a camera, which may also be described herein as a camera portion of the endoscope. The camera may have a wireless interface, or may be wired, to provide power and/or data transfer capabilities to the camera, and may thus be connected to a display screen. Examples of such endoscopes are known in the art. In certain embodiments, as discussed in more detail below in connection with FIGS. 6A and 6B, a sheath encasing a fiber optic cable can be inserted through the first tube 12 and the first tube 12 may be fitted to connect to the endoscope in a locking manner (e.g., using a screw-type or snapping-type connector at the proximal end that attaches to the endoscope). As a result, a lens element of an endoscope may be positioned at a distal end of the first tube 12. Thus, the first tube 12 may be outfitted with a camera holding mechanism to connect to a camera and to house part of an endoscope. When the endoscope is attached to and partly inserted through the first tube 12, endoscope combined with the first tube 12 may be referred to as an endoscope portion of arthroscopic equipment.

The second lumen may be outfitted with a system for housing and manipulating one or more tools. For example, one or more surgical tools, such as a grabber, a suture cutter, a suture passer, a crochet hook, a punching device, etc., may be connected to and included within the second lumen and may be extendable outside and retractable inside of a first, distal end of the lumen to be used for surgical procedures. To manipulate these tools, one or more manipulation devices may extend outside of a second, proximal end of the lumen. The second lumen combined with any attached tools may be referred to as a tool portion of arthroscopic equipment.

As such, the cannula may have a proximal end at which manipulation devices for one or more surgical tools may be attached and located, and at which part of an endoscopea may attach, and a distal end at which the surgical tools may be attached and located and at which a distal end of the endoscope, such as camera lens, may be located. Examples depicting these ends will be described in greater depth below.

In one embodiment, the two tubes are attached to each other, such that the second tube, in which the tools are disposed, piggy-backs on the first tube, in which the endoscope is inserted. The two tubes may together be referred to as a housing, which together house part of an endoscope and one or more tools. A distal end of the endoscope and one or more tools may be disposed at a distal end of the housing, and a manipulation device may be disposed at a proximal end of the housing. In one embodiment, the two tubes are connected such that their outside surfaces contact each other and/or are parallel to each other at first portions (e.g., at corresponding respective distal ends), but at second portions (e.g., corresponding respective proximal ends), the second tube, which may be referred to herein as the tool tube, secondary cannula, or actuator tube extends away (e.g., diverges) from the first tube, which may be referred to herein as the camera tube, scope tube or main cannula. In this manner, the cannula, at its distal end, can be inserted as a single piece into and through a single portal of a patient's body, and tools can then be manipulated and the surgical area can be viewed by holding and/or manipulating the endoscope and tool tube by a single hand. Further, the manipulation devices associated with and connected to the tool tube may therefore be manipulated by one or more fingers and/or a thumb of the operator's hand, while the same hand (e.g., palm of the hand and/or other fingers or thumb) holds and/or moves an endoscope inserted through the camera tube, thereby selectively positioning the endoscope.

In certain embodiments, the tool tube may be configured to attach to and house a single tool. Thus, at least a first tool may be connected to the tool tube at the distal end of the tool tube. For example, in some embodiments, the tool tube may be equipped with a single tool, which may be, for example connected to a manipulation device such as a knob, which manipulates the tool via actuation. In this manner, the knob can be pressed and held in place with a finger or thumb in order to push the tool outside of the distal end of the tool tube for performing operations (e.g., scraping, pushing, cutting, etc.). Thus, the manipulation device and first tool may be arranged so that the first tool can be moved in relation to the tool tube by manipulation of the manipulation device by the single hand. In some embodiments, the tool may be connected to the manipulation device, for example, in a spring-loaded manner, so that the distance at which it extends beyond an end of the tool tube can be controlled with precision by an operator.

In some embodiments, the spring loading may cause the tool to remain inside the tool tube in a default position (e.g., when no pressure is placed on it), and then an operator can push down (e.g., with a pad of a finger or thumb) on the manipulation device to move the tool to be different distances beyond the distal end of the tool tube. Based on the amount of pressure, the tool can be extended to a desired distance beyond the distal end of the tool tube. A more detailed description of a spring loading system is described below in connection with FIGS. 3 and 7.

In some embodiments, the spring loading may be combined with some resistance and/or with locking mechanisms at one or more lengths, so that the surgical tool can be maintained at a particular distance with respect to the distal end of the tool tube without the need for an operator to exert continuous downward pressure. For example, a mechanism including a locking device, such as used with a ball-point pen, may be used (e.g., allowing push spring and lock, and push spring and disengage motions). In one embodiment, a locking device is used that permits the tool to be maintained in a locked position extending beyond the distal end of the tool tube. Examples of such a system can be seen, for example, in U.S. Pat. Nos. 2,734,484, 3,084,670, 3,819,282, 5,263,786, and 6,280,110, each of which is incorporated herein by reference in its entirety. These patents describe a pen or pencil spring loaded locking device. Such a device or a similar mechanism can be used to implement the locking mechanism of the spring loaded tool described above in connection with the tool tube. For example, a rigid wire connected to the tool can be manipulated by a manipulation device at the proximal end of the tool tube, and can be locked in an extended position, using a locking mechanism such as disclosed in one of these patents.

In some embodiments, a rotatable component can be used as the manipulation device, such that an operator can rotate the surgical tool using the rotatable component, with just one finger or thumb, or with one or two fingers and/or a thumb. For example, a knob used for manipulation of the tool may be rotatable (e.g., it may be in the shape of a circular wheel, or a hexagonal nut, or any other shape rotatable about an axis). The manipulation device may be connected to the tool using a wire, for example, which may be rotatable within the second tube. For example, the wire may be a rigid wire that rotates the same amount as the manipulation device. This allows a greater range of operations to be performed, particularly if both a spring-loaded and a rotatable tool are used.

For example, in one embodiment, using a spring-loaded, rotatable knob, the manipulation device and first tool are arranged so that the first tool can be both rotated and moved forward and backward in relation to the tool tube by manipulation of the manipulation device by the single hand.

In some embodiments, more than one tool can be housed within the tool tube. For example, a mechanism such as used in a pen-type exchange system may be used to allow different tools to be selected simply with the pressing of one or more manipulation devices at the proximal end. Examples of such exchange systems can be seen in U.S. Pat. Nos. 2,071,510, 2,826,173, 2,849,983, 3,266,465, 4,227,822, and 4,268,183, which are each hereby incorporated by reference herein in their entirety. Or a plurality of tool tubes may be included with a single scope tube. In these manners, an operator can switch between tools in order to operate on a patient, with a single hand, leaving the other hand available to hold another tool, such that a single operator can perform procedures, such as cutting, scraping, suturing, etc., without the need for second person to be holding an endoscope.

The distal end of the cannula may be referred to as a port-insertion portion. A diameter of the first tube at the port-insertion portion may be one of various diameters, based on particular surgery being performed. In addition, the diameter of the second tube at the port-insertion portion may be smaller, for example by a factor of-about 2-5 times smaller than that of the first tube (e.g., in some embodiments, about ⅓ the diameter). For example, in certain embodiments, the diameter of the first tube at the port-insertion portion may be about 4 mm to about 9 mm for shoulder surgery, about 2.5 mm to about 3.5 mm for wrist surgery, or about 7 mm to about 8.3 mm for knee surgery. The diameters for the second tubes may be about 2-5 times smaller, for example. These are examples only, and other diameters and ratios may be used that allow for an operation to be safely and properly performed.

For spring-loaded devices, in certain embodiments, each tool may be configured along with its manipulation device and a component such as a wire connecting the two, such that the tool may be extended a certain distance beyond a distal end of the second tube. For example, in one embodiment, tools may be extended up to about ½ inch beyond the terminal end of the second tube. However, these are examples only, and other distances may be used that allow for an operation to be safely and properly performed.

Figure 2:
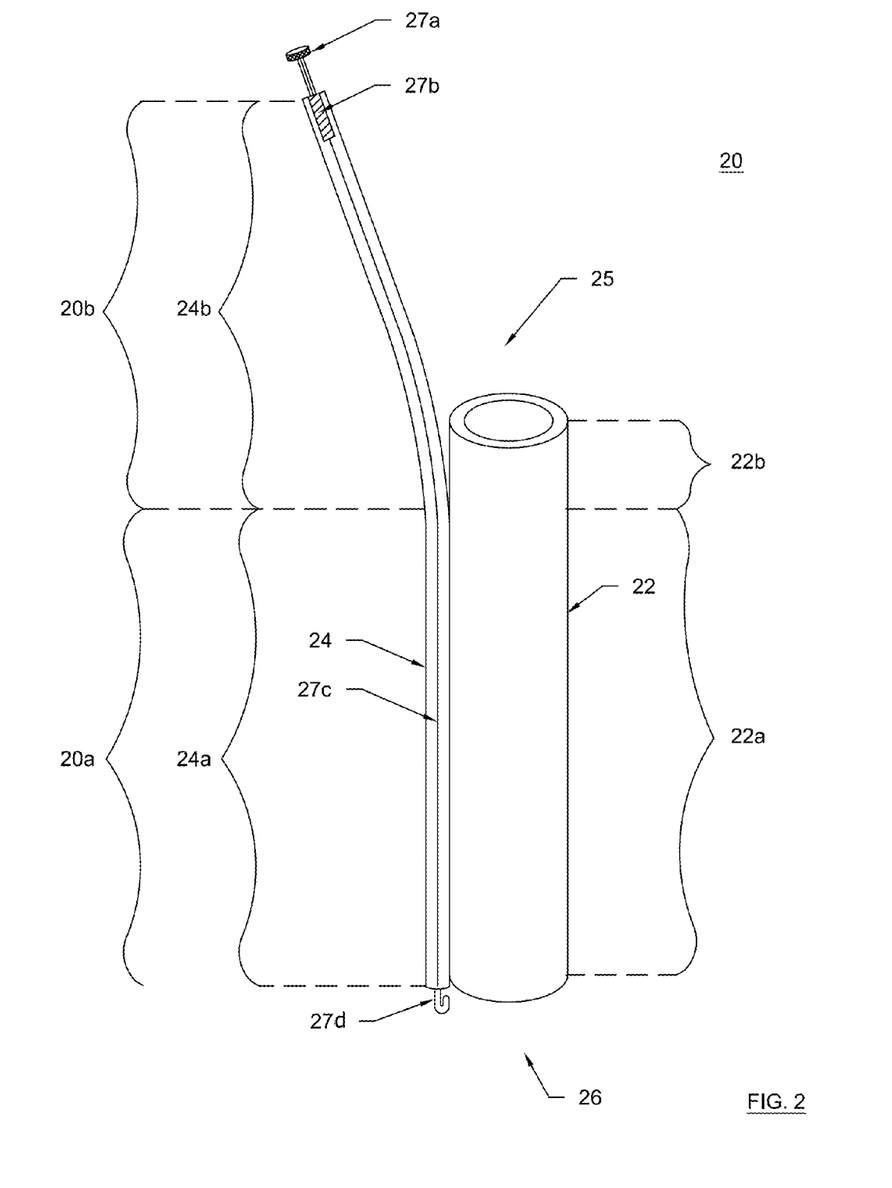
FIG. 2 depicts an exemplary cannula according to certain exemplary embodiments.

An exemplary cannula 20 according to certain embodiments is shown in FIG. 2. For example, the cannula 20 may have a rigid structure, with the first tube 22 and second tube 24 adjacent and parallel along their outer lengthwise surfaces at a first portion 20*a*, and with the first tube 22 and second tube 24 separated from each other and diverging from each other at a second portion 20*b*. The first tube may be described as including a first portion 22*a* that corresponds to first portion 20*a* of the cannula 20 and a second portion 22*b* that corresponds to second portion 20*b* of the cannula, and the second tube may be described as including a first portion 24*a* that corresponds to first portion 20*a* of the cannula 20 and a second portion 24*b* that corresponds to second portion 20*b* of the cannula.

The first portion 20*a* of the cannula 20 may be referred to as a tube-aligned portion or tube-together portion, and the second portion 20*b* of the cannula 20 may be referred to as a tube-separated, or tube-apart portion. As can be seen in FIG. 2, in certain embodiments, at a distal end 26 of the cannula 20, the first tube 22 and second tube 24 may contact each other, and at a proximal end 25 of the cannula 20 (proximal and distal ends described in relation to portions corresponding to an operator and a subject respectively), the first tube 22 and second tube 24 may be separate from each other and do not contact each other. In certain embodiments, the proximal end 25 of the second tube 24 may be curved away from the first tube 22. The proximal end of 25 of the second tube 24 may also extend beyond the proximal end of the first tube 22.

FIG. 2 also shows an exemplary tool system 27a-27d, including a manipulation device 27a, a spring loading system 27b, a connector 27c, such as a wire, and a tool 27d. Manipulation device 27a may be, for example, a knob having one of many shapes (e.g., wheel, hexagonal nut, etc.). The manipulation device 27a may connect to a connector 27c, such as wire. The manipulation device 27a may be connected to the connector 27c at a proximal end 25 of the second tube 24. In certain embodiments, the manipulation device 27a connects to the connector 27c through a spring loading system 27b. The tool 27d may be connected to the connector 27c at a distal end 26 of the second tube 24. The tool 27d may be an attachable/detachable tool, or may be permanently affixed to an end of the connector 27c.

In certain embodiments, the manipulation device 27a, connector 27c, and tool 27d may all be rotatable in relation to the second tube 24, to allow for more versatile manipulation of the tool 27d. Thus, the connector 27c may be formed of a material that has a relative high rigidity such that it retains its length and is substantially inelastic when rotated pushed, or pulled, but is flexible enough in a rotation direction to conform to the shape of the tool tube, yet rigid enough to hold the tool 27d in a fixed position in relation to the manipulation device 27a. In certain embodiments, the spring loading system 27b may cause the tool 27d to remain inside the tool tube 24 in a default position (e.g., when no external pressure is placed on it), and then an operator can push down (e.g., with a pad of a finger or thumb) on the manipulation device 27a to move the tool to be different distances beyond the distal end 25 of the tool tube 24. Based on the amount of pressure, the tool 27d can be extended to a desired distance beyond the distal end 26 of the tool tube 24.

Figure 3:
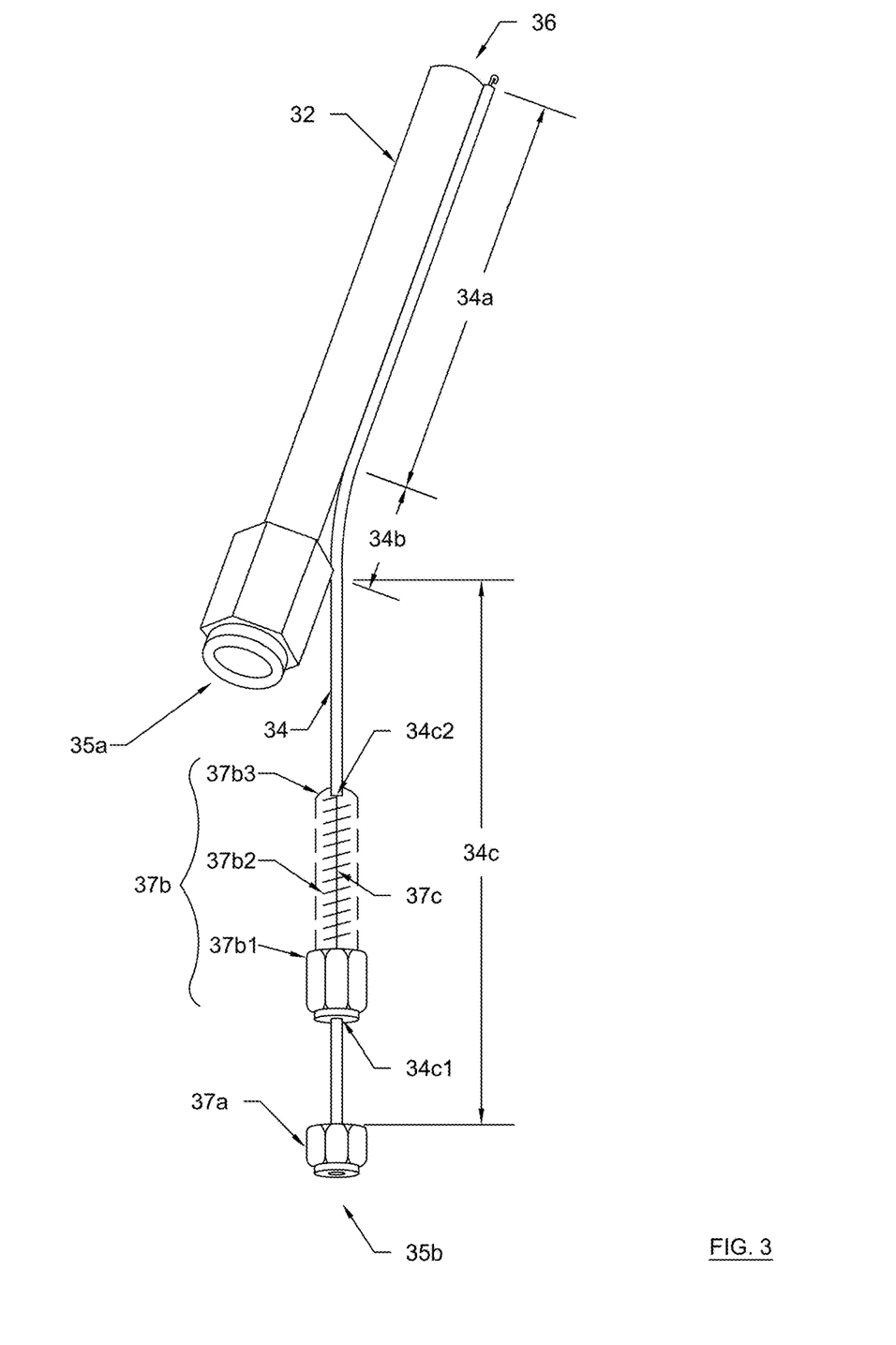
FIG. 3 depicts an exemplary cannula according to certain exemplary embodiments.
Figure 8:
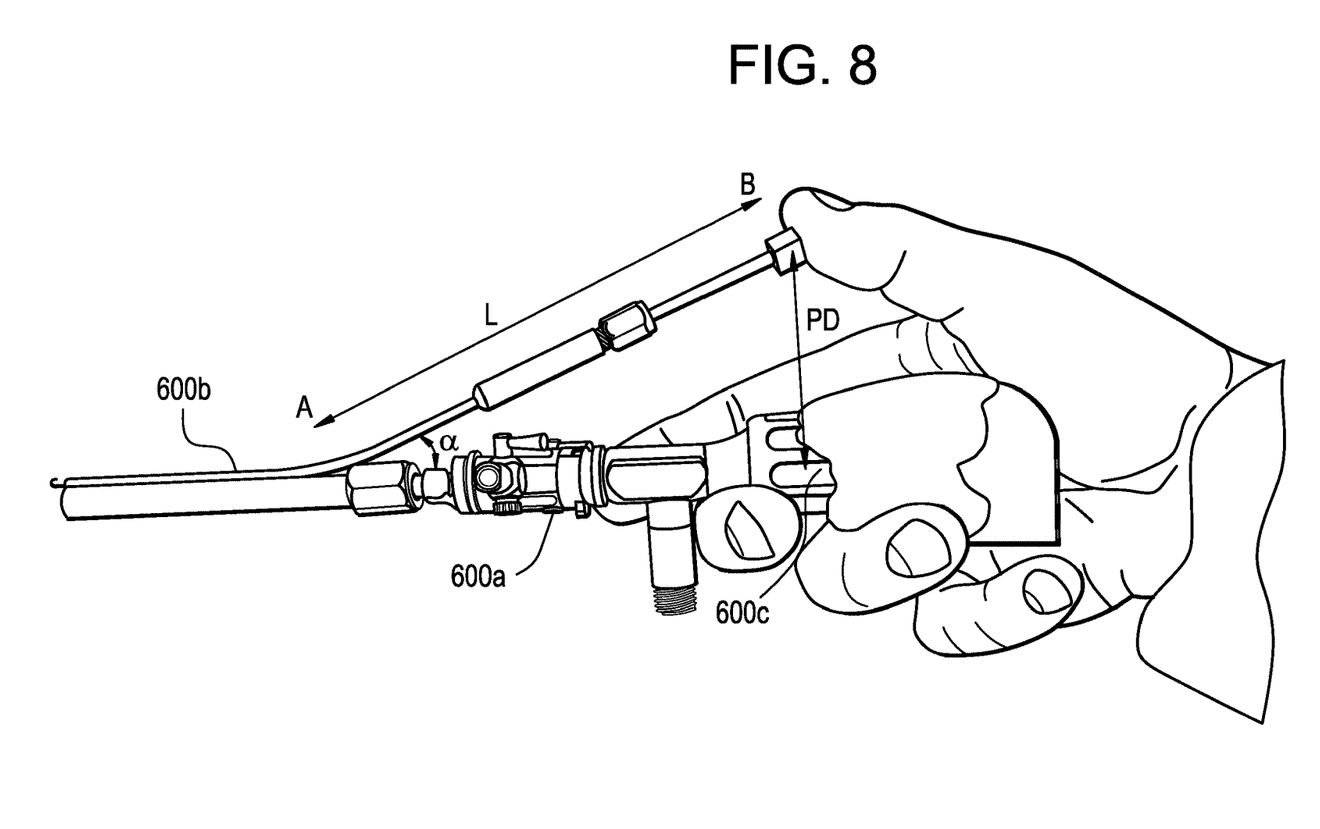
FIG. 8 is a picture depicting an example of a cannula attached to an endoscope and including a tool being manipulated by a single hand of an operator, according to certain exemplary embodiments.

Another exemplary embodiment of a cannula is described FIG. 3. In certain embodiments, as depicted in FIG. 3, the second tube 34 may include three portions, or sections. A first portion 34a may be a straight portion that contacts the first tube 32. A second portion 34b may be curved or bent away from the first tube 32. A third portion 34c may be straight and at a particular angle with respect to the first tube 32. In certain embodiments, the third portion 34c may also extend beyond a proximal end 35a of the first tube 32, such that a proximal end 35b of the second tube 34 extends beyond a proximal end 35a of the first tube 32. An angle between the first portion 34a and third portion 34c of the second tube 34 may be, for example, between about 15 and 35 degrees, or in some embodiments between about 5 and 35 degrees. In some embodiments, the length of portion 34a may be between about 7 cm and 10 cm, and the length of portion 34c may be between about 15 cm and 22 cm. FIG. 8 depicts this latter distance as "L." Thus, according to the geometry of these ranges, in some embodiments, a perpendicular distance from a line extending from the first portion 34a to a proximal end of the third portion 34c (e.g., the proximal end of a tool manipulation system connected to the second tube 34, where knob 37a is located) may be between about 3.9 cm and 12.6 cm. FIG. 8 depicts this distance as "PD." However, these lengths and angles may vary and should not be thought as limiting the scope of the invention. In some embodiments, the length of portion 34c paired with the angle between the first portion 34a and third portion 34c of the second tube 34 are of such values (e.g., within the example ranges above) that allow for a single operator's hand to both hold an endoscope camera with part of one hand and to manipulate the knob 37a with the same hand. For example, a distance PD for an average hand having about 20 cm between extended thumb and pinky finger may be between about 5 and 10 cm. Smaller hands may benefit from a slightly smaller distance PD, such as 4 cm, and larger hands may benefit from a slightly larger distance PD, such as 12 cm.

The first tube 32 may have a straight shape, and may be outfitted to house part of an endoscope so that the first tube 32 functions as part of an endoscope. Any known endoscope devices may be used, such as those made by Olympus®, Stryker®, or Storz®. In certain embodiments, the second tube 34 may be attached to and/or integrated with a rigid tube of a known endoscope.

As shown in the example of FIG. 3, the second tube 34 may include a tool manipulation system (e.g., shown by 37a-37c) for performing surgical procedures. For example, the tool manipulation system may include a knob 37a, an adjustment system 37b, and a connector 37c. In some embodiments, a tool (not shown) can be connected to the connector 37c. In some embodiments, a tool (not shown) is included as part of the tool system. The knob 37a may be in the form of a hexagonal nut, or may be in a circular form. In one example embodiment the knob 37a includes serrated edges for better grip. The knob 37a may be connected to a connector 37c. The connector 37c may be, for example a wire fixedly attached to the knob 37a. In one embodiment, if the knob 37a is rotated, then the connector 37c also rotates. The adjustment system 37b may also be connected to the connector 37c. In one embodiment, for example, the adjustment system 37b is a spring-loaded adjustor that adjusts the connector 37c in relation to the second tube 34. The adjustment system 37b may include, for example, an anchor 37b1 attached to a first separated internal end 34c1 of the third portion 34c of the second tube 34, a spring 37b2 located between a second separated internal end 34c2 of the third portion 34c of the second tube 34 and the anchor 37b1, and a cylindrical outer casing 37b3 connected at one end to the anchor 37b1 and slidably engaged with the outer surface of the second tube 34 at a second opposite end.

The second tube 34 may have a rib or other device to maintain a separation between the spring 37b2 and an end of the outer casing 37b3, such that when no pressure is exerted on the knob 37a, the tool system remains at a default extension. This default extension may be an extension at which a tool (not shown in FIG. 3) remains inside the second tube 34. By pressing on the knob 37a, the tool is caused to be extended past a distal end of the second tube 34. The adjustment system 37b allows the tool to be extended and retracted in a controlled manner.

In certain embodiments, the knob 37a is fixedly attached to the connector 37c, and the connector 37c is fixedly or removably attached to a tool at the distal end of the second tube 34. The knob 37a may be rotatable such that the tool may be rotated to allow for more versatile control of the tool based on manipulation of the knob 37a.

In addition, in certain embodiments, a locking mechanism may be used along with the adjustment system 37b, so that one or more different locked extension lengths of a tool beyond a distal end 36 of the second tube 34 may be set. For example, a lock and release system such as used in ball-point pens and described above may be used for the adjustment system 37b to allow for at least one fixed extension length of the tool. As a specific example, an end of the outer casing 37b3 that engages with the second tube 34 can have certain grooves that engage with notches (not shown) on the second tube 34. The grooves and notches can be curved in a way to allow for locking in a manner similar to that used in one or more of the various pen/pencil systems described above. As such, the outer casing 37b3 may be rotatably affixed to the anchor 37b1. In this manner, the cannula may support rotation of the tool, forward and backward movement of the tool, and locking of the tool at a particular distance beyond a distal end of the tool tube 34.

Though a spring is depicted in FIG. 3, particularly as being at a specific location along with the accompanying components of the adjustment system 37b, the exact configuration of an adjustment system can be varied. For example, similar to certain pen-type mechanisms, such as described in certain patents such as listed above (see, e.g., U.S. Pat. No. 2,734,484, incorporated by reference herein in its entirety), part of the adjustment system may be located at a proximal end of the tool tube of the cannula, and part of the adjustment system (e.g., a spring and certain other components) can be located at a distal end of the tool tube.

Figure 4:
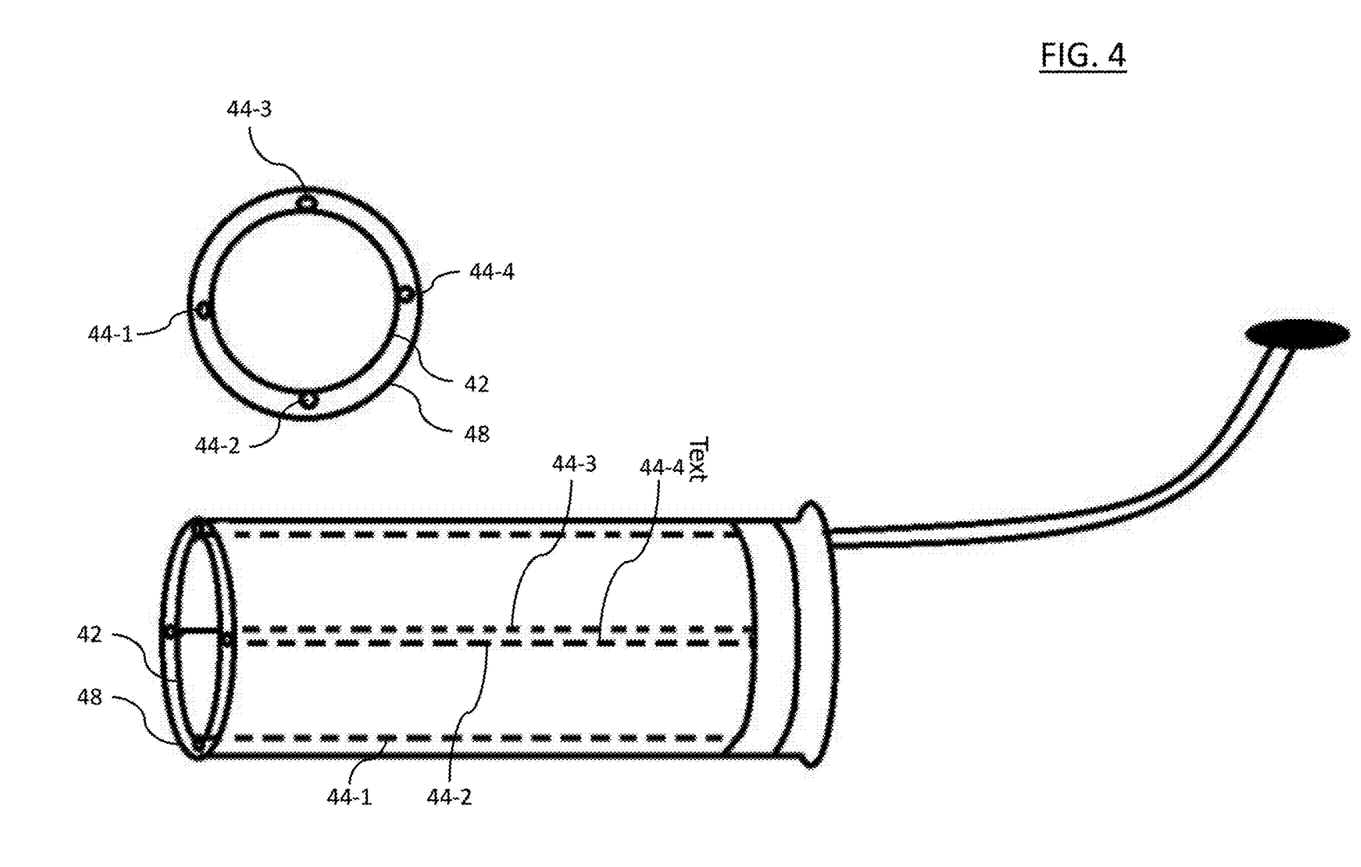
FIG. 4 depicts an exemplary cannula according to certain exemplary embodiments.

FIG. 4 depicts a cannula according to certain exemplary embodiments. As shown in FIG. 4, the cannula 40 can have a single scope tube 42, but a plurality of tool tubes 44-1, 44-2, 44-3, 44-4, etc. Each tool tube may house a different tool. Details of the components that form each tool tube are omitted for brevity. But in certain embodiments, each tool tube may have a structure and operation similar to or the same as one or more of the various embodiments discussed above in connection with FIGS. 1-3. An outer casing 48 may be formed to surround the scope tube 42 and plurality of tool tubes 44-1 through 44-4. Spaces between the scope tube 42 and outer casing 48 between the various tool tubes may be filled with a filler material. As a result, the outer surface of the cannula 40 may be smooth as it coincides with the outer surface of the outer casing 48. Though not shown, the cannula assemblies depicted in FIGS. 1, 2, and/or 3 may also include a similar outer casing 48.

In certain embodiments, the cannula 50 may house a plurality of tools, but unlike in FIG. 4, the plurality of tools may be housed in a single tool tube. The single tool tube may allow for the exchange of tools, for example using a tool exchange system similar to those used in exchangeable ball-point pen systems as discussed above in connection with certain patents incorporated by reference herein.

In use, a cannula such as described in the figures above may allow an operator (e.g., a doctor, surgeon, etc.) to control both an endoscope and a surgical tool with a single hand. An example of this is depicted in FIG. 8, which also depicts the length A-B (corresponding to the length of 34c shown in FIG. 3), the angle α (corresponding to the angle discussed above in connection with FIG. 3), and the distance PD (described previously), which can be derived from the length A-B and angle α. For example, in one embodiment, the operator can hold a camera portion of an endoscope, attached at a proximal end of the tube-together portion (e.g., 20a in FIG. 2 and similar portions in FIGS. 1 and 3-5) of the cannula by the palm of a hand on the end of the camera portion and wrapping the operator's fingers around sides of the camera portion, and the operator can then use the thumb of the same hand to manipulate (e.g., extend, retract, and rotate) a surgical tool, or multiple surgical tools, of the tool tube of the cannula. This can be accomplished without the operator removing the single hand from the arthroscopic equipment, and without the assistance of a second hand. In addition, because the tool tube and scope tube may be fixedly attached to each other, the manipulation of the tool in relation to the cannula and camera may be carried out without the tool housing (e.g., tool tube) and endoscope housing (e.g., scope tube) being moved in relation to each other. While doing so, the operator can use his or her other hand to manipulate a second tool or object, so that procedures requiring the use of a first surgical tool (e.g., suture cutter, suture passer, grabber, scraper, crochet hook, etc.), a second surgical tool or object (e.g., sutures, punching tool, etc.), and an endoscope, can be performed by a single operator. This can be particularly useful in certain types of surgeries that involve tight spaces, where having two people in close proximity may cause difficulties.

Figure 5:
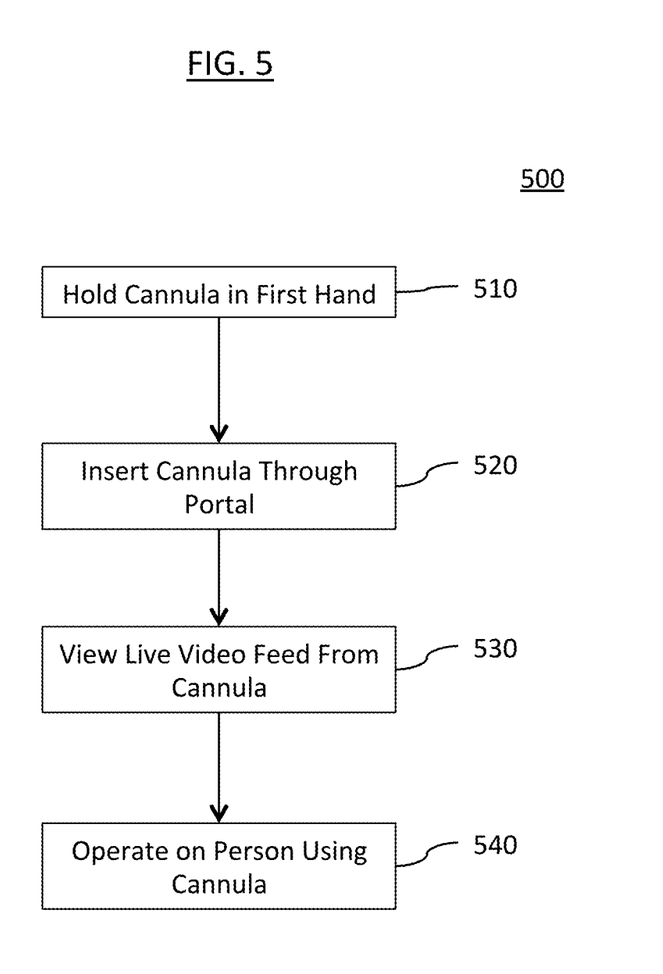
FIG. 5 is a flow chart depicting a surgical procedure according to certain exemplary embodiments.

An example of a surgical procedure is described in connection with FIG. 5. As shown in FIG. 5, a surgical procedure 500 can include, for example, a biopsy wherein a sample of human flesh is removed from a patient, arthroscopic surgery for removing and/or repairing damaged ligaments, tendons, etc., or other known surgical procedures for which arthroscopes are typically used. The surgical procedure may be performed using a cannula such as described above in the various embodiments. For example a cannula with a first tube housing an endoscope and second, piggy-backing tube housing one or more tools, such as described above in connection with FIGS. 1-4 may be used. In certain embodiments, the cannula may be held in a first hand (step 510). For example, a surgeon or doctor may hold the endoscope and tool with a single hand. The doctor's other hand may be free to use additional tools, or for other purposes.

In one embodiment, the camera of the endoscope is connected to conventional computer equipment connected to a display screen, so that the doctor can view a live video feed generated by the camera. As mentioned above, the scope tube of the cannula may also include a light that illuminates the area being operated on. An exemplary camera, light, endoscope, computer system, and display are all known in the art, and thus details thereof are not described herein.

In step 520, a distal end of the cannula is inserted through a portal in a person. For example, while still holding the cannula in the first hand, the doctor may insert the distal end of the cannula through the portal, so that an inside of the person's body can be both viewed and operated on using the cannula. As such, a live video image received from an endoscope portion (e.g., a lens) disposed at the inserted distal end of the cannula can be viewed (step 530). Further, while viewing the live video image, the doctor can use a tool of the cannula, still held with the same single hand, to perform an operation on the person (step 540). For example, flesh can be cut from the person, sutures can be put into the person (e.g., in some embodiments using the endoscope and tool with the same single hand along with a suture held by a different hand), etc. As such, while viewing the live video image, the tool of the cannula can be manipulated with the same first hand with respect to the cannula to perform the operation on the person. The manipulation may include, for example, rotating the tool with respect to the cannula, moving the tool forward and/or backward with respect to the cannula, and/or locking the tool in an extended position. As described above, manipulation of the tool may be implemented without removing the first hand from the cannula.

Figure 6A:
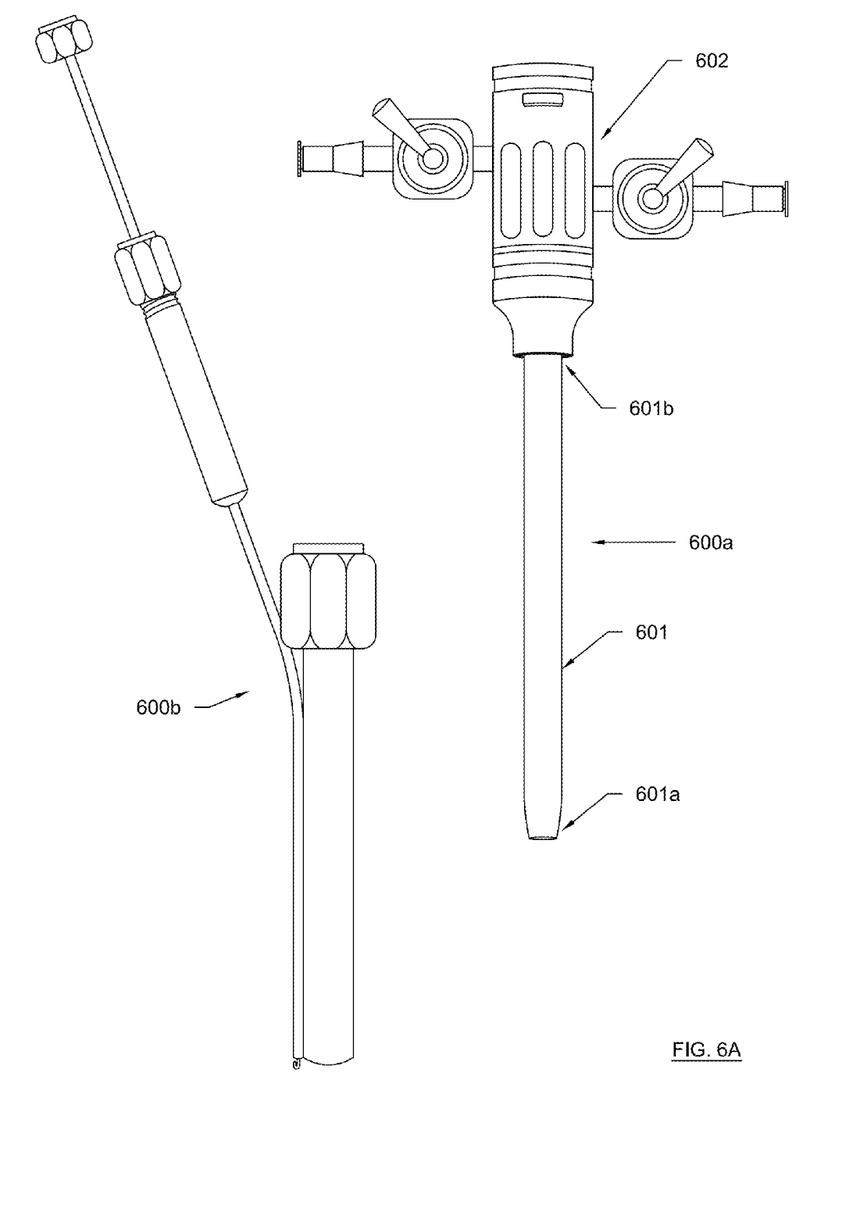
FIGS. 6A and 6B show examples of part of an attachment for an endoscope according to certain exemplary embodiments.
Figure 6B:
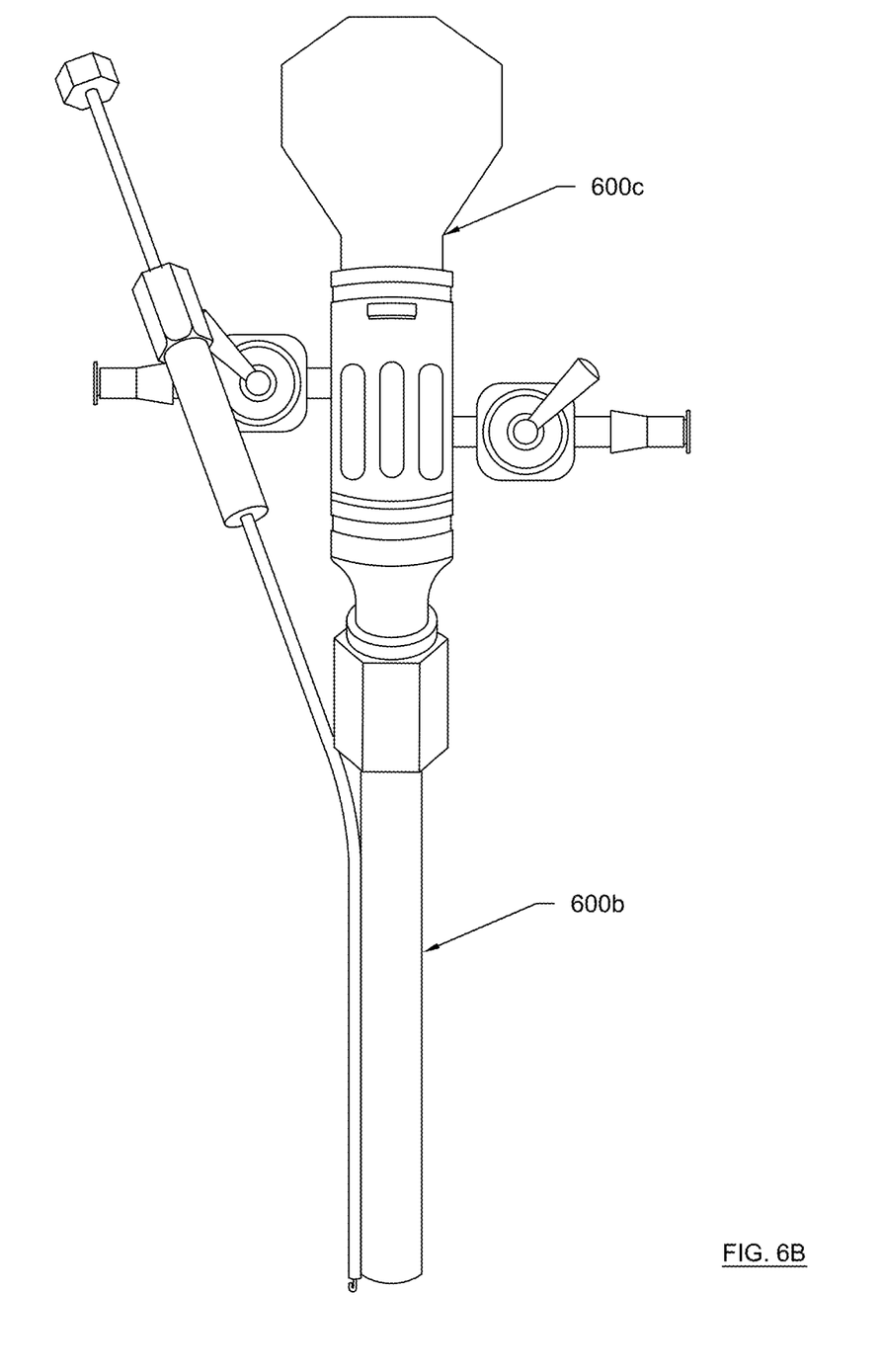

FIGS. 6A and 6B show examples of part of an attachment 600a for an endoscope. The attachment may connect an endoscope to a cannula (labeled 600b) such as described in one or more of FIGS. 1-4. For example, as shown in FIG. 6A, an attachment for an endoscope may include a sheath 601 having a distal end 601a and a proximal end 601b, and a connector portion 602. The sheath 601 may be for housing a fiber optic portion of an endoscope, wherein a distal end of the endoscope (e.g., housing a lighting element and a lens) is located at the distal end of the sheath 601a. The connector portion 602 may connect between the sheath 601 and a camera apparatus (not shown), which may include, for example, image capture electronics and a wire or other device for electronically transmitting images to a screen for real-time viewing by medical professional, such as a doctor performing surgery.

FIG. 6B shows an example where the endoscope (labeled 600c) may be attached to the cannula (labeled 600b) such as shown in one of FIGS. 1-4. The endoscope 600c may include, for example, a camera apparatus, fiber optic cable, light source, and lens, as discussed previously. A fiber optic cable, light source, and lens may be housed by the scope tube of the cannula, and a tool system may be housed by the tool tube. The endoscope 600c may connect to the cannula 600b using an attachment, such as attachment 600a shown in FIG. 6A. For example, the attachment 600a may have various threading that matches threading of the endoscope 600c and threading of the cannula 600b to allow for secured connection between the devices. In some embodiments, the endoscope may be pre-configured to include a sheath and connection portion, and an endoscope so outfitted may then connect with the cannula such as described in the various figures herein. In certain embodiments, the distal end of the scope tube may have a partly or mostly covered tip so that tissue and other fluids are prevented from entering the cannula.

In certain embodiments, the top of the endoscope may include a light element, a lens element, and one or more sucking or spraying holes through which fluids and/or tissue can be sucked or sprayed into the patient. Other than the holes, the tip may be sealed. In some embodiments, the scope tube (e.g., 12, 22, 32, etc.) may have a tip that corresponds to the endoscope tip, such that the tip is sealed other than one or more holes corresponding to sucking or spraying holes of the endoscope tip. In certain embodiments, the distal end of the scope tube may have a skirt through which the distal tip of an endoscope extends, and which prevents fluids from entering or exiting the internal space between the scope tube of the cannula and the endoscope.

Figure 7:
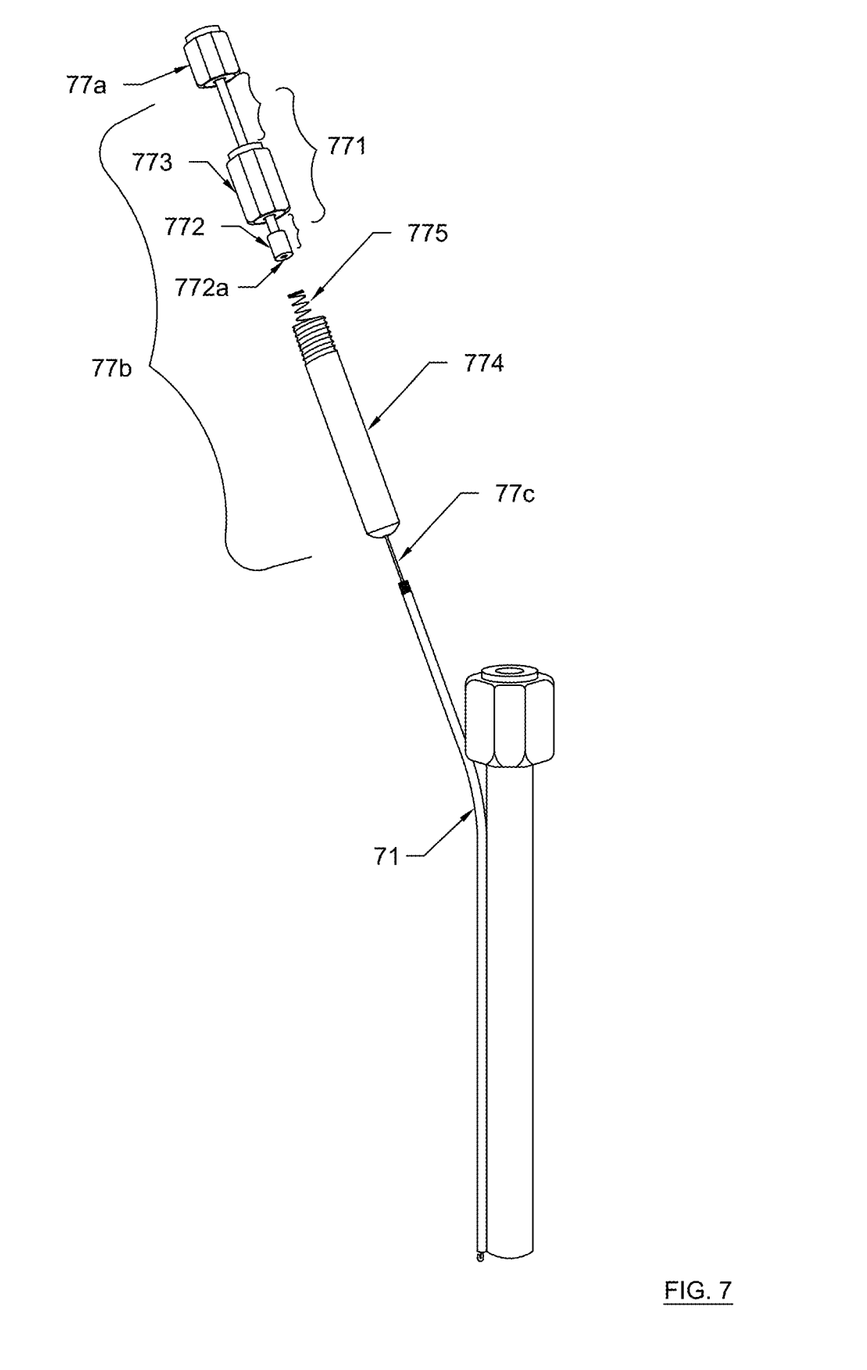
FIG. 7 is an exploded view showing an example of a cannula according to certain exemplary embodiments.

FIG. 7 is an exploded view showing an example of a cannula showing additional aspects according to certain exemplary embodiments. As shown in the example of FIG. 7, the second tube 71 may form part of a tube assembly including a tool manipulation system 77 at a proximal end for performing surgical procedures. For example, the tool manipulation system may include a knob 77a, an adjustment system 77b, and a connector 77c. In some embodiments, a tool (not shown) can be connected to the connector 77c, which may be for example, a wire. In some embodiments, a tool (not shown) is included as part of the tool system. The knob 77a may be in the form of a hexagonal nut, or may be in a circular form. In one example embodiment the knob 77a includes serrated edges for better grip. These are only examples, however, and other shapes and gripping mechanisms can be used. The knob 77a may be connected to a rod 771 having a head 772 on the end opposite the knob 77a. The head 772 may have a hole (772a) on one end into which a connector 77c (e.g., a wire) may be inserted and secured.

A nut 773 having threading may be formed around the rod 771. The nut 773 may couple to a casing 774 surrounding the connector 77c using the threading. The casing 774 may connect at one end to the nut 773 and at an opposite end to an end of tool tube 71, for example via corresponding threadings. Though threadings are given as example, other connecting mechanisms may be used. A spring 775 may be placed between the head 772 and an inside of the casing 774. For example, the inside of the casing (not shown) may include a rib for supporting the spring 775. As such, the spring may extend and contract between the rib and the head 772, so that when the connector 77c is attached to the head 772, the tool at the distal end of the connector 77c is connected in a spring loaded manner and can be moved back and forth between a default contracted position within the tool tube 71 to an extended position outside of the tool tube 71.

In one embodiment, the knob 77a may be rotatable and may have a fixed connection to one end of a connector 77c such as a wire. In this manner, in addition to a tool being moved forward and backward in relation to a distal end of the tool tube 71, the tool can also be rotated, to allow for additional versatility during an operation or surgery.

It should be noted that in some embodiments, the cannula having a tool tube and scope tube may be formed as shown, for example, in FIG. 6A, wherein the scope tube is configured to receive a sheath of an attachment to an endoscope, and the tool tube is connected to an outside of the scope tube. In these embodiments, the cannula may be designed to retrofit existing endoscope attachments such as item 600a shown in FIG. 6A. Thus, the cannula may allow for two-hand, two-tool arthroscopic surgery without the need to alter any existing endoscope equipment. In other embodiments, a tool tube such as shown in FIG. 6A may be connected directly to a sheath of the attachment for the endoscope, so that the sheath connected to a tool tube makes up the cannula assembly described herein (e.g., the sheath may form the scope tube described herein).

The various embodiments described herein are for the purposes of illustration only, and are not intended to be limiting on the invention. For example, though specific examples of orthopedic surgery are described in the background section, the various embodiments of a cannula assembly described herein can be used for other surgeries as well. Various modifications may be made to the above example embodiments, with the proper scope of protection being referenced in the following claims.

What is claimed is:

1. A method of performing an arthroscopic surgical procedure using a cannula,
the cannula including a first tube housing an arthroscope and a second tube piggybacked on the first tube and housing a first tool, the first tube including a rigid structure formed of a tubular wall, wherein a proximal end of the tubular wall remains parallel to a distal end of the tubular wall during the arthroscopic surgical procedure, and a proximal portion of the second tube extends away from the first tube and includes a manipulation system for moving the first tool relative to the second tube,
the manipulation system including:
an end piece configured for linear movement between a first position which causes a distal end of the first tool to be disposed within the second tube and a second position which cause the distal end of the first tool to project distally beyond the second tube; a casing fixed to a proximal end of the second tube, the end piece projecting proximally from the casing; and an adjustor disposed inside the casing and configured to bias the end piece to the first position;

the method of performing the arthroscopic procedure including:
  inserting the cannula, arthroscope, and first tool within a joint of a patient using a first hand of a person;
  manipulating the first tool relative to the second tube within the joint by depressing the end piece of the manipulation system with the first hand from the first position to the second position while simultaneously gripping the arthroscope with the first hand.

2. The method of claim 1, wherein the adjustor includes a spring.

3. The method of claim 1, the method further comprising:
at the same time as depressing the end piece of the manipulation system with the first hand, using a second tool or object held with a second hand of the person to operate on the joint.

4. The method of claim 1, wherein the cannula is detachable from the arthroscope.

5. The method of claim 1, further comprising:
rotating the end piece to further manipulate the first tool.

6. The method of claim 1, further comprising:
during the arthroscopic surgical procedure, locking the first tool at a particular distance beyond a distal end of the second tube.

7. The method of claim 1, wherein the end piece is a knob.

8. The method of claim 7, further comprising:
rotating the knob to further manipulate the first tool.

9. The method of claim 7, further comprising:
at the same time as depressing the knob of the manipulation system with the first hand, using a second tool or object held with a second hand of the person to operate on the joint.

* * * * *